United States Patent [19]
Yokoyama et al.

[11] Patent Number: 5,994,592
[45] Date of Patent: Nov. 30, 1999

[54] PROCESS FOR PRODUCING 2,2'-BIS(HYDROXYMETHYL)ALKANAL AND 2,2'-BIS(HYDROXYMETHYL)ALKANOIC ACID

[75] Inventors: Toshiharu Yokoyama; Kouji Maeda, both of Kanagawa-ken, Japan

[73] Assignee: Nippon Kasei Chemical Company Limited, Fukushima-ken, Japan

[21] Appl. No.: 09/022,725

[22] Filed: Feb. 12, 1998

[30] Foreign Application Priority Data

Feb. 19, 1997 [JP] Japan ..................................... 9-034773
Nov. 18, 1997 [JP] Japan ..................................... 9-316906

[51] Int. Cl.⁶ .................................................... C07C 47/26
[52] U.S. Cl. .......................... 568/464; 568/460; 568/461; 568/497; 562/523
[58] Field of Search .................... 568/464, 460, 568/461, 497, 853, 854, 860, 868, 878, 879; 562/523, 580, 531, 552, 590, 593

[56] References Cited

U.S. PATENT DOCUMENTS 3,312,736  4/1967  Ruhf ........................................ 260/530
4,233,247  11/1980  Immel et al. ............................ 568/464

FOREIGN PATENT DOCUMENTS 0004577  10/1979  European Pat. Off. .
2301505  9/1976  France .
2385670  10/1978  France .
1535826  12/1978  United Kingdom .

OTHER PUBLICATIONS

Derwent Abstract No. AN 98–046929 & JP 09 295 956 (Nov. 18, 1997).
Derwent Abstract No. AN 91–296364 & DD 290 006 (May 16, 1991).
Vik, "Studies on Intermediates Involved in the Syntheses of Pentaerythritol and Related Alcohols. V.* On the Kinetics of the Base–catalyzed Aldol Condensation Reactions of Intermediate Aldehydes with Formaldehyde", Acta Chemica Scandinavica B28 (1974) pp. 325–332.

*Primary Examiner*—Shailendra Kumar
*Assistant Examiner*—Sreeni Padmanabhan
*Attorney, Agent, or Firm*—Dilworth & Barrese

[57] ABSTRACT

The present invention relates to a process for producing 2,2'-bis(hydroxymethyl)alkanal and 2,2'-bis(hydroxymethyl)alkanoic acid as raw materials for dimethylol alkanoic acids or trimethylol alkanes, which are useful for the production of polyesters, polyurethanes, alkyd resins and the like, in an industrially advantageous manner.

17 Claims, 1 Drawing Sheet

PROCESS FOR PRODUCING 2,2'-BIS (HYDROXYMETHYL)ALKANAL AND 2,2'-BIS(HYDROXYMETHYL)ALKANOIC ACID

BACKGROUND OF THE INVENTION

The present invention relates to a process for producing 2,2'-bis(hydroxymethyl)alkanal and 2,2'-bis(hydroxymethyl)alkanoic acid. More particularly, the present invention relates to a process for producing 2,2'-bis(hydroxymethyl)alkanal and 2,2'-bis(hydroxymethyl) alkanoic acid as raw materials of dimethylol alkanoic acids or trimethylol alkanes, which are useful raw materials for the production of polyesters, polyurethanes, alkyd resins or the like, in an industrially advantageous manner.

It is well known in the art that 2,2'-bis(hydroxymethyl) alkanals have been produced by reacting aliphatic aldehyde with formaldehyde in the presence of a basic substance.

As the basic substances used in the above-mentioned production of 2,2'-bis(hydroxymethyl)alkanals, there have been proposed various substances such as sodium hydroxide (Japanese Patent Publication (KOKOKU) No. 52-20965 (1977) and Japanese Patent Application Laid-open (KOKAI) No. 62-263141(1987)), sodium carbonate (U.S. Pat. No. 3,312,736), triethylamine (Japanese Patent Publication (KOKOKU) No. 4-55181(1992)) or dimethylamino neopentanol (German Patent No. 2507461).

In these conventional processes, since formaldehyde is used in approximately stoichiometric amount, i.e., in such an amount that the molar ratio of formaldehyde to aliphatic aldehyde is about 2, a considerable amount of 2-substituted acrolein is produced as a by-product, thereby causing difficulty in producing the desired 2,2'-bis(hydroxymethyl) alkanals in industrially advantageous.

On the contrary, when formaldehyde is used in such an increased amount of not less than 10 equivalents based on an equivalent amount of aliphatic aldehyde in order to inhibit the production of 2-substituted acrolein as a by-product, the desired 2,2'-bis(hydroxymethyl)alkanals can be produced with a high yield. However, in this case, an excess amount of formaldehyde remains unreacted, so that it is necessary to subsequently conduct complicated procedures for removal or recycling of the excess amount of residual formaldehyde, resulting in an increase in the production cost. Further, in the case where such an excess amount of formaldehyde remains in the alkanal as the desired product, there also arises the problem that a large amount of expensive oxidizing agent must be added to the reaction mixture in the subsequent oxidation step or otherwise an undesirable side reaction will occur therein.

That is, when aliphatic aldehyde and formaldehyde are charged in a molar ratio of 1:2 to 1:10 and reacted with each other in the presence of a base catalyst, a considerable amount of 2-substituted acrolein is disadvantageously produced as a by-product together with the desired 2,2'-bis(hydroxymethyl)alkanal. The amount of 2-substituted acrolein produced as a by-product is varied depending upon the kind of aliphatic aldehyde used, the kind and amount of base catalyst used, the reaction temperature or the like. For instances, when n-butyl aldehyde is reacted with formaldehyde at a temperature of about 60° C. in the presence of triethylamine, 2-ethyl acrolein is produced in an amount as large as about 20 mole %. It is also known that the 2-substituted acrolein is produced by dehydration of 2-hydroxymethylalkanal which is a precursor of 2,2'-bis(hydroxymethyl)alkanal, and there exists equilibrium between 2-hydroxymethylalkanal and the 2-substituted acrolein. Therefore, where the molar ratio of aliphatic aldehyde to formaldehyde charged is small, the production of the 2-substituted acrolein as a by-product cannot be avoided.

On the other hand, the 2-substituted acrolein can be converted into 2,2'-bis(hydroxymethyl)alkanal as the desired product by reacting with formaldehyde in the presence of a base catalyst and water. However, in order to obtain the desired product with a high yield, it is required to use formaldehyde in an excess amount of from 10 to 30 moles per mole of the 2-substituted acrolein. As described above, in this case, a large amount of formaldehyde remains unreacted, so that additional steps are required to separate the residual formaldehyde from the desired product, resulting in an industrially disadvantageous process.

In addition, as methods for converting the 2-substituted acrolein by-product into 2,2'-bis(hydroxymethyl)alkanal, include those various methods mentioned below. In Japanese Patent Application Laid-open (KOKAI) No. 52-124213 (1977), there has been proposed a method of producing 2,2'-bis(hydroxymethyl)butanal by reacting 2-ethyl acrolein with an aqueous formaldehyde solution in the presence of triethylamine. However, in this method, a considerable excess amount of formaldehyde relative to 2-ethyl acrolein is requires thus resulting in an increase in production cost.

In German Patent No. 2507461 (British Patent No. 1,535, 826), there has been proposed a process which comprises a first step of reacting n-butyl aldehyde with formaldehyde in a reactor, for example, in the presence of N,N-dimethylamino neopentanol, followed by removing unreacted n-butyl aldehyde and 2-ethyl acrolein as a by-product from the reaction solution by distillation, and a second step of adding formaldehyde and amine to the resultant distillate to react with each other. However, the German Patent is wholly silent about not only control or adjustment of the molar ratio between the 2-substituted acrolein and formaldehyde in the reaction system, but also control or adjustment of the molar ratio between aliphatic aldehyde and formaldehyde. Further, in the process of the German Patent, formaldehyde is used in approximately stoichiometric amount, resulting in low yield of the desired product as described hereinbefore. This also indicates that the process of the German Patent is not industrially advantageous.

Furthermore, it is known in the art that 2,2'-bis(hydroxymethyl)alkanal is converted into dimethylol alkanoic acid by oxidation and into trimethylolalkane by hydrogenation.

As the methods of producing 2,2'-bis(hydroxymethyl) alkanoic acid by the oxidation of 2,2'-bis(hydroxymethyl) alkanal, there have been proposed a method of conducting the oxidation using hydrogen peroxide (e.g., U.S. Pat. No. 3,312,736), a method of conducting the oxidation in the presence of at least one compound catalyst selected from the group consisting of cerium, titanium, zirconium, tin, niobium, molybdenum and tungsten using hydrogen peroxide (Japanese Patent Application Laid-open (KOKAI) 62-263141(1987)) and a method of conducting the oxidation using perisobutyric acid (Journal of Institute of Organic Synthesis Chemistry, 36, 1095(1978)), or the like. However, in these conventional methods in which 2,2'-bis(hydroxymethyl)alkanal produced by known methods is subjected to oxidation, there arise problems that the yield of 2,2'-bis(hydroxymethyl)alkanal is low, and that since a large amount of residual formaldehyde is contained in the reaction solution, it is necessary to add a large amount of an oxidizing agent thereto in the subsequent oxidation step. As a result, it becomes impossible to obtain the desired product with a high purity and a high yield.

That is, heretofore methods capable of producing 2,2'-bis (hydroxymethyl)alkanal with a high yield, and reducing the amount of residual formaldehyde in the reaction solution have been unknown.

It has now been discovered herein that by reacting aliphatic aldehyde with formaldehyde in the presence of a base catalyst and reacting the resultant 2-substituted acrolein by-product with a specific amount (molar ratio) of formaldehyde in the presence of a base catalyst while controlling or adjusting amounts (molar ratio) of aliphatic aldehyde and formaldehyde to be charged to within specified values, the amount of residual formaldehyde in the reaction solution can be considerably reduced and the desired 2,2'-bis (hydroxymethyl)alkanal can be produced with a high yield in an industrially advantageous manner.

SUMMARY OF THE INVENTION

It is an object of the present invention to provide a process for producing 2,2'-bis(hydroxymethyl)alkanal, which reduce a larger burden of the additional process for the recovery of unreacted formaldehyde, and can considerably reduce the amount of residual formaldehyde, thereby enabling the desired 2,2'-bis(hydroxymethyl)alkanal to be produced with a high yield in an industrially advantageous manner.

To accomplish the foregoing object, in a first embodiment of the present invention, there is provided a process for producing 2,2'-bis(hydroxymethyl)alkanal represented by the general formula (II):

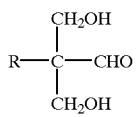

(II)

wherein R is a substituted or unsubstituted aliphatic hydrocarbon group, by reacting aliphatic aldehyde represented by general formula (I):

RCH$_2$CHO            (I)

wherein R is a substituted or unsubstituted aliphatic hydrocarbon group, with formaldehyde in the presence of a base catalyst, which process comprises:
(i) reacting aliphatic aldehyde of the general formula (I) with a formaldehyde-containing solution in the presence of a base catalyst to produce 2,2'-bis (hydroxymethyl)alkanal and as a by-product 2-substituted acrolein represented by the general formula (III):

(III)

wherein R is a substituted or unsubstituted aliphatic hydrocarbon group; and
(ii) reacting the 2-substituted acrolein (III) produced in step (i) with formaldehyde in the presence of a base catalyst in a molar ratio of 2-substituted acrolein (III) to formaldehyde of 1:3 to 1:100 to produce 2,2'-bis (hydroxymethyl)alkanal,
the molar ratio of aliphatic aldehyde (I) to formaldehyde totally charged into the overall process being in the range of 1:1 to 1:5.

In a second embodiment of the present invention, there is provided a process for producing 2,2'-bis(hydroxymethyl) alkanal represented by the general formula (II):

(II)

wherein R is a substituted or unsubstituted aliphatic hydrocarbon group, by reacting aliphatic aldehyde represented by general formula (I):

RCH$_2$CHO            (I)

wherein R is a substituted or unsubstituted aliphatic hydrocarbon group, with formaldehyde in the presence of a base catalyst, which process comprises:
(i) reacting aliphatic aldehyde represented by general formula (I) with a formaldehyde-containing solution in the presence of a base catalyst to produce 2,2'-bis (hydroxymethyl)alkanal and a 2-substituted acrolein represented by the general formula (III):

(III)

wherein R is a substituted or unsubstituted aliphatic hydrocarbon group,
(ii) separating 2-substituted acrolein (III) from the reaction mixture of step (i);
(iii) reacting separated 2-substituted acrolein (III) with formaldehyde in the presence of a base catalyst in a molar ratio of the 2-substituted acrolein (III) to formaldehyde of 1:3 to 1:100 to produce a formaldehyde-containing reaction mixture containing 2,2'-bis(hydroxymethyl)alkanal; and
(iv) reacting at least a portion of the formaldehyde-containing reaction mixture obtained in the step (iii) with the aliphatic aldehyde represented by the general formula (I) in the presence of a base catalyst to produce 2,2'-bis(hydroxymethyl)alkanal,
the molar ratio of aliphatic aldehyde to formaldehyde totally charged into the overall process being in the range of 1:1 to 1:5.

In a third embodiment of the present invention, there is provided a process for producing 2,2'-bis(hydroxymethyl) alkanal represented by the general formula (II):

(II)

wherein R is a substituted or unsubstituted aliphatic hydrocarbon group, by reacting aliphatic aldehyde represented by the general formula (I):

RCH$_2$CHO            (I)

wherein R is a substituted or unsubstituted aliphatic hydrocarbon group, with formaldehyde in the presence of a base catalyst, which process comprises:

(i) reacting aliphatic aldehyde represented by the general formula (I) with a formaldehyde-containing solution in the presence of a base catalyst to produce 2,2'-bis(hydroxymethyl)alkanal and as a by-product 2-substituted acrolein represented by the general formula (III):

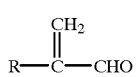

wherein R is a substituted or unsubstituted aliphatic hydrocarbon group; and (ii) reacting a 2-substituted acrolein (III) produced in step (i) with formaldehyde in the presence of a base catalyst in a molar ratio of 2-substituted acrolein (III) to formaldehyde of 1:3 to 1:100 to produce 2,2'-bis(hydroxymethyl)alkanal, the molar ratio of aliphatic aldehyde to formaldehyde totally charged into the overall process being in the range of 1:1 to 1:5, a portion of the reaction mixture produced in step (i) being separated into a component which is rich in 2,2'-bis(hydroxymethyl)alkanal and a component which is rich in 2-substituted acrolein, and the component which is rich in 2-substituted acrolein being reacted with formaldehyde in the presence of a base catalyst, followed by introducing the resultant reaction mixture to step (i), thereby continuously producing 2,2'-bis(hydroxymethyl)alkanal.

DETAILED DESCRIPTION OF THE INVENTION

Figure 1:
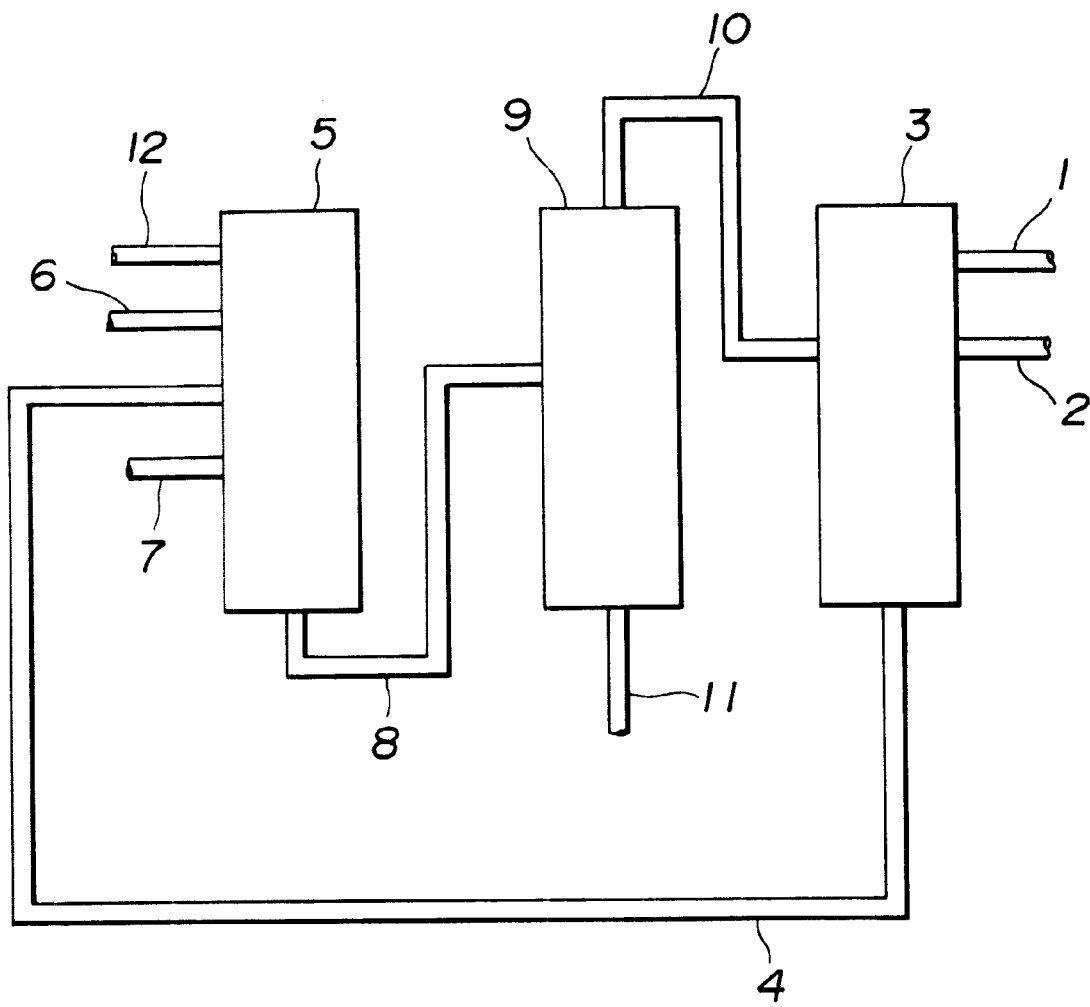
FIG. 1 is a flow chart showing an embodiment of a continuous reaction system used for the production of 2,2'-bis(hydroxymethyl)alkanal according to the present invention.

The present invention is described in detail below.

In the present invention, any known procedure can be used for the afore-mentioned aldehyde reaction step and 2-substituted acrolein reaction step provided the molar ratio of the aliphatic aldehyde to the formaldehyde totally charged into the overall process is in the range of 1:1 to 1:5, and preferably, the said steps constitute a circulation system.

Specifically, one embodiment of the a process comprises:

(a) an aldehyde reaction step (i) of reacting the aliphatic aldehyde represented by aforementioned general formula (I) with a formaldehyde-containing solution in the presence of a base catalyst to produce 2,2'-his (hydroxymethyl)alkanal;

(b) a step (ii) of separating a fraction containing 2-substituted acrolein produced as a by-product in the aldehyde reaction step (i) and represented by the general formula (III):

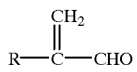

wherein R is a substituted or unsubstituted aliphatic hydrocarbon group, from the reaction solution separated from the above aldehyde reaction step (i);

(c) a 2-substituted acrolein reaction step (iii) of reacting the fraction containing 2-substituted acrolein with formaldehyde in the presence of a base catalyst in a molar ratio of the 2-substituted acrolein to formaldehyde of 1:3 to 1:100 to produce 2,2'-bis(hydroxymethyl)alkanal; and (d) a step (iv) of reacting at least a part of the formaldehyde-containing reaction solution obtained in the above 2-substituted acrolein reaction step (iii) with aliphatic aldehyde represented by the general formula (I) in the presence of a base catalyst to produce 2,2'-bis(hydroxymethyl)alkanal.

In the afore-mentioned process, the reaction step (iv) is identical to the reaction step (i) in which the formaldehyde-containing reaction solution obtained in the 2-substituted acrolein reaction step (iii) is used as the formaldehyde-containing solution of the aldehyde reaction step (i). It is preferred that steps (i) to (iii) be repeatedly conducted, because the process can then be simplified and construction cost of the plant can be reduced.

The substituent group R of each of the general formulae (I) to (III) may include hydrocarbon groups having 1 to 16 carbon atoms, preferably 1 to 7 carbon atoms.

Typical examples of the substituent groups are linear or branched alkyl groups. The alkyl groups may be substituted by an alkoxy group having 1 to 4 carbon atoms which is inert under the reaction conditions. Examples of the alkoxy substituent groups may include methoxy, ethoxy, propoxy, butoxy and the like. Examples of suitable alkyl groups may include methyl, ethyl, n-propyl, iso-propyl, n-butyl, iso-butyl, n-pentyl, n-hexyl, n-heptyl, iso-hexyl, dodecyl and pentadecyl. Among them, methyl, ethyl n-propyl and iso-propyl are especially preferred.

The aliphatic aldehyde of general formula (I) used in the present invention include aldehydes to whose α-carbon atom two hydrogen atoms are bonded. Examples of suitable aliphatic aldehydes include propionaldehyde, n-butyl aldehyde, iso-butyl aldehyde, n-pentyl aldehyde, iso-pentyl aldehyde, n-hexyl aldehyde, iso-hexyl aldehyde, n-heptyl aldehyde, iso-heptyl aldehyde, n-octyl aldehyde, iso-octyl aldehyde, n-nonyl aldehyde, iso-nonyl aldehyde, dodecyl aldehyde, pentadecyl aldehyde and the like. Among them, aliphatic aldehydes having 3 to 9 carbon atoms are especially preferred.

As the formaldehyde used in the present invention, water-diluted formaldehyde, i.e., an aqueous formaldehyde solution, may be suitably used because it is easy to handle. The aqueous formaldehyde solution may contain formaldehyde in an amount of preferably 5 to 60% by weight, more preferably 30 to 55% by weight. Among them, an aqueous formalin solution is especially preferred.

As the base catalysts used in the steps (i), (iii) and (iv) of the process according to the present invention, there may be exemplified those described in Japanese Patent Applications Laid-open (KOKAI) Nos. 52-124213(1977) and 4-55181 (1992), German Patent Nos. 947,419 and 2,507,461, U.S. Pat. No. 3,312,736 and British Patent No. 1,317,106. Specific examples of the base catalysts may include hydroxides or carbonates of alkali metals, hydroxides or carbonates of alkali earth metals, tertiary amines, basic ion exchangers and the like. These basic substances may be used singly or in the form of a mixture of any two or more thereof.

Examples of useful hydroxides or carbonates of alkali metals may include sodium hydroxide, sodium carbonate, sodium bicarbonate, potassium hydroxide, potassium carbonate, potassium bicarbonate and the like. The base catalysts used in the respective steps may be the same or different.

Tertiary amine compounds that may be used as the base catalyst include aliphatic, alicyclic or heterocyclic amines having 3 to 20 carbon atoms, preferably 3 to 15 carbon atoms. Among them, aliphatic tertiary amines are preferred. Examples of useful tertiary amines include symmetric trialkylamines such as trimethylamine, triethylamine, tri-n-propylamine, tri-iso-propylamine, tri-n-butylamine, tri-iso-butylamine or tri-tert-butylamine; asymmetric trialkylamines such as methyldiethylamine, dimethylethylamine, ethyl-di-iso-propylamine or dimethyl-tert-butylamine; diamines such as N,N-tetramethylethylenediamine or triethylenediamine; N,N-dimethylcyclohexylamine, bis(2-hydroxyethyl)-cyclohexylamine, N-methylpyrrolidine, N-methylpiperidine or N-methylmorpholine; amines having substituent groups such as N,N-dimethylaminoethanol or N,N-dimethylaminoneopentanol; aromatic ring-containing amines such as tribenzylamine or N,N-dimethylbenzylamine; polyamines having a tertiary amino group such as triethylenediamine or bis(2-dimethylaminoethyl)methylamine; tetraalkyl ammonium hydroxides such as tetraethyl ammonium hydroxide; and the like. Among them, trialkylamines are preferred.

When the afore-mentioned aliphatic aldehyde and formaldehyde are subjected to a condensation reaction in the presence of the base catalyst, dimethylolalkanal (i.e., 2,2-bis(hydroxymethyl)alkanal) represented by the above general formula (II) can be produced. In this case, when propionaldehyde is used as the raw aliphatic aldehyde, dimethylolpropanal is produced, whereas when n-butyl aldehyde is used as the raw aliphatic aldehyde, dimethylolbutanal is produced.

The 2-substituted acroleins represented by general formula (III) include 2-alkyl acroleins which are produced as a by-product of the reaction between the aliphatic aldehyde of general formula (I) and formaldehyde. Examples of the 2-alkyl acroleins include 2-methyl acrolein, 2-ethyl acrolein, 2-propyl acrolein, 2-butyl acrolein, 2-pentyl acrolein, 2-hexyl acrolein and the like.

In the process according to the present invention, the reaction between the aliphatic aldehyde represented by the general formula (I) and formaldehyde is carried out under the specified condition that the molar ratio of the aliphatic aldehyde to formaldehyde totally charged to the overall process is in the range of 1:1 to 1:5. It is preferred that the molar ratio fall in the range of 1:1 to 1:3, since this allows the amount of residual formaldehyde in the desired 2,2'-bis(hydroxymethyl)alkanal to be reduced.

The process according to the present invention may be carried out, for example, in the following manner.

After the aldehyde reaction step (i), at least a portion of the resulting reaction solution is supplied to a separation column where 2,2'-bis(hydroxymethyl)alkanal as the desired product and 2-substituted acrolein as a by-product are separated from each other. The separated 2-substituted acrolein is introduced into a separate reaction vessel to which a base catalyst and formaldehyde are supplied. In the reaction vessel, the 2-substituted acrolein and formaldehyde are reacted with each other, thereby providing a reaction solution containing 2,2'-bis(hydroxymethyl)alkanal and unreacted residual formaldehyde (the 2-substituted acrolein reaction step (iii)). The thus-obtained reaction solution may be supplied into a separation column to separate 2,2'-bis(hydroxymethyl)alkanal as the desired product. Alternatively, the reaction solution obtained in step (iii) may be supplied into the reaction vessel of the aldehyde reaction step (i) for repeated use. On the other hand, the reaction solution separated from the separation column which is rich in 2,2'-bis(hydroxymethyl)alkanal as the desired product is supplied to a subsequent oxidation step.

In reaction step (iii) in which the 2-substituted acrolein contained in the fraction is reacted with formaldehyde, the molar ratio of the 2-substituted acrolein charged to formaldehyde charged is preferably in the range of 1:3 to 1:100, more preferably 1:3 to 1:50. In the step (i) of the process according to the present invention, the molar ratio of the 2-substituted acrolein produced to the aliphatic aldehyde charged is influenced by the molar ratio of formaldehyde charged to the aliphatic aldehyde charged. Therefore, the molar ratio of the aliphatic aldehyde to the 2-substituted acrolein both exiting in the step (i) is preferably in the range of 1:0.01 to 1:2, more preferably 1:0.05 to 1:1.

Where the amount of the 2-substituted acrolein produced in step (i) is small, the effect of the present invention cannot be expected because the amount of the desired product produced from the 2-substituted acrolein in step (iii) is also small.

Further, where the amount of 2-substituted acrolein produced is small, since it is intended that formaldehyde be used in an excess amount relative to that of the aliphatic aldehyde, additional procedures are required to remove the residual formaldehyde thereby rendering the process industrially disadvantageous.

The amount of base catalyst used in step (iii) of the process according to the present invention is usually in the range of 0.01 to 1.0 mole, preferably 0.02 to 0.5 mole per mole of the 2-substituted acrolein. In addition, the amount of the base catalyst used in the step (i) or (iv) is in the range of 0.01 to 1.0 mole, preferably 0.02 to 0.5 mole per mole of the aliphatic aldehyde used therein.

In the reactions carried out in the process according to the present invention, an inert organic solvent may be added to the respective reaction systems in order to enhance the solubility of the aliphatic aldehyde or the 2-substituted acrolein in the aqueous formaldehyde solution. Examples of the inert organic solvents include lower aliphatic alcohols such as methanol, ethanol, propanol and isopropanol; aliphatic or alicyclic ethers such as diethyl ether, tetrahydrofuran and dioxane; and the like.

The reaction conditions used in steps (i), (iii) and (iv) may, if desired, be nearly the same.

The reaction temperature is varied depending upon the kind and amount of base catalyst used. For example, where inorganic compounds such as alkali metals and alkali earth metals are used as the base catalyst, the reaction temperature is in the range of about $-10°$ C. to about $100°$ C., preferably about $10°$ C. to about $80°$ C. In addition, tertiary amines are used as the base catalyst, the reaction temperature is in the range of about $-10°$ C. to about $120°$ C., preferably about $10°$ C. to about $100°$ C. The reactions of the process according to the present invention may be carried out under ordinary pressure but may also be carried out under elevated pressure or reduced pressure.

As methods of separating the 2-substituted acrolein as a by-product from the reaction solution obtained in step (i), there may be used a distillation method, a solvent extraction method or a combination thereof. Among them, the distillation method is preferred. The fraction containing the 2-substituted acrolein which is separated form the reaction solution obtained in step (i) may contain the 2-substituted acrolein in an amount of 30 to 100% by weight, preferably 50 to 100% by weight. The fraction may contain, in addition to the 2-substituted acrolein, unreacted aliphatic aldehyde, unreacted formaldehyde, water, methanol, the base catalyst and the like.

The process according to the present invention may be carried out by using either a batch method, a semi-continuous method or a continuous method.

The semi-continuous method means, for example, such a method comprising a step of reacting aliphatic aldehyde with formaldehyde (step (i)); a step of separating the fraction containing the 2-substituted acrolein from the reaction solution obtained in step (i) (step (ii)); a step of reacting the fraction containing the 2-substituted acrolein with formaldehyde (step (iii)); and a step of reacting the resultant reaction solution containing residual formaldehyde with the aliphatic aldehyde (step (iv)) in which each step may be carried out in a batch or continuous manner, and may be sequentially and repeatedly conducted.

The continuous method is such a method in which the reactions of the respective steps are continuously carried out.

An example of the continuous method or the semi-continuous method is explained below by referring to FIG. 1. Aldehyde reaction vessel 5 is supplied with aliphatic aldehyde through conduit 6 and with formaldehyde used at the beginning of reaction through conduit 12. The aliphatic aldehyde and formaldehyde are reacted with each other in the presence of a base catalyst. The resultant reaction solution is fed into separation column 9 through conduit 8 and separated into a fraction which is rich in 2-substituted acrolein and a fraction which is rich in 2,2'-bis(hydroxymethyl)alkanal as the desired product. The thus-obtained fraction containing 2-substituted acrolein is supplied into acrolein reaction vessel 3 through conduit 10. Acrolein reaction vessel 3 is separately supplied with formaldehyde through conduit 1 and with a base catalyst through conduit 2 to react the 2-substituted acrolein with formaldehyde. The fraction which is rich in 2,2'-bis(hydroxymethyl)alkanal as the desired product is supplied through conduit 11 into subsequent steps, for example, a purification step, an oxidation step, a hydrogenation step or the like. The resultant reaction solution extracted from acrolein reaction vessel 3 contains 2,2'-bis(hydroxymethyl)alkanal as the desired product and residual formaldehyde. The reaction solution is fed back to the aldehyde reaction vessel 5 through conduit 4. Into aldehyde reaction vessel 5 to which the aliphatic aldehyde is continuously supplied, a required amount of the base catalyst is supplied through conduit 7 to continue the reaction between the aliphatic aldehyde and formaldehyde.

The 2,2'-bis(hydroxymethyl)alkanal produced according to the present invention may be converted into trimethylol alkane or dimethylol alkanoic acid by known methods.

As the methods of obtaining 2,2'-bis(hydroxymethyl)alkanoic acid by the oxidation of 2,2'-bis(hydroxymethyl)alkanal, there can be used the afore-mentioned known methods, i.e., conducting the oxidation using hydrogen peroxide (e.g., U.S. Pat. No. 3,312,736), conducting the oxidation in the presence of a catalyst selected from cerium, titanium, zirconium and the like using hydrogen peroxide (Japanese Patent Application Laid-open (KOKAI) 62-263141(1987)), conducting the oxidation using perisobutyric acid (Journal of Institute of Organic Synthesis Chemistry, 36, 1095(1978)), and the like. Of these methods, the oxidation by hydrogen peroxide is preferred.

As the methods of producing trimethylol alkane by the hydrogenation of 2,2'-bis(hydroxymethyl)alkanal, a method of conducting the hydrogenation in the presence of a hydrogenation catalyst such as Ni, Cu, Pt or Pd as described hereinbefore can be used.

In accordance with the present invention, by effectively utilizing the 2-substituted acrolein as a by-product, the desired 2,2'-bis(hydroxymethyl)alkanal can be produced with a high yield even though the amount of formaldehyde used for the polycondensation with aliphatic aldehyde is small. For this reason, the load required to recover unreacted formaldehyde can be reduced, thereby realizing an industrially valuable process.

The present invention will now be described in more detail with reference to the following examples and comparative examples, but the present invention is not restricted to those examples and various modifications are possible within the scope of the invention.

EXAMPLE 1

42.9 g (500 mmol) of 35% aqueous formaldehyde solution and 12 g (167 mmol) of n-butyl aldehyde were supplied into 100 ml round bottom flask equipped with a reflux condenser. While heating the mixed solution at 40° C., 1.7 g (16.8 mmol) of triethylamine was added dropwise thereto. While maintaining the temperature of the mixed solution at 40° C., the reaction between n-butyl aldehyde and formaldehyde was conducted for one hour (reaction step (i)). At this time, the molar ratio between n-butyl aldehyde, formaldehyde and triethylamine charged was 1:3:0.1.

The percentage of conversion of n-butyl aldehyde was 99.8%; the total yield of 2,2'-bis(hydroxymethyl)butanal and a formaldehyde adduct of 2,2'-bis(hydroxymethyl)butanal was 62.4 mole %; and the selectivity to the desired products was 62.5%. The formaldehyde adduct of 2,2'-bis(hydroxymethyl)butanal can be converted into dimethylol butanic acid as a desired final product in subsequent steps such as an oxidation step.

In the above reaction, the yield of 2-ethyl acrolein was 17.2 mole %. In addition, the amount of residual formaldehyde was 45.4 mole % based on the mole of n-butyl aldehyde.

Further, the reaction solution obtained by reacting n-butyl aldehyde with formaldehyde was subjected to distillation at 90° C. under ordinary pressure to separate a fraction containing 2-ethyl acrolein therefrom (concentration: 98% by weight).

Next, the thus-separated fraction containing 2.33 g (27.7 mmol) of 2-ethyl acrolein was added to 35.7 g (416 mmol) of 35% aqueous formaldehyde solution. While heating the mixed solution to 40° C., 0.28 g (2.77 mmol) of triethylamine was added dropwise into the mixed solution. Thereafter, the mixed solution was maintained at 40° C. for one hour to react 2-ethyl acrolein and formaldehyde with each other (reaction step (iii)). At this time, the molar ratio between 2-ethyl acrolein, formaldehyde and triethylamine charged was 1:15:0.1.

In the above reaction, the yield of 2,2-bis(hydroxymethyl)butanal was 55.2 mole %, the yield of formaldehyde adduct of 2,2'-bis(hydroxymethyl)butanal was 8.8 mole %, and the total yield thereof was 63.9 mole % based on the weight of 2-ethyl acrolein.

Next, while maintaining the temperature of the reaction solution obtained in reaction step (iii) at 40° C., 10 g (139 mmol) of n-butyl aldehyde is added to the reaction solution. Thereafter, 1.12 g (11 mmol) of triethylamine was added dropwise into the mixed solution, and then n-butyl aldehyde and the unreacted formaldehyde were reacted with each other at 40° C. for one hour (reaction step (iv)). This reaction step (iv) is regarded as identical to the reaction step (i) in which the reaction solution obtained in the reaction step (iii) was used as the formaldehyde component in the reaction step (i).

In reaction step (iv), the percentage of conversion of n-butyl aldehyde was 97.5%; the total yield of 2,2'-bis (hydroxymethyl)butanal and the formaldehyde adduct of 2,2'-bis(hydroxymethyl)butanal was 75.8 mole %; and the total selectivity thereto was 77.7%. At that time, the yield of 2-ethyl acrolein was 16.6 mole % which was nearly identical to the yield thereof obtained in reaction step (i) only. Further, the amount of residual formaldehyde was 58 mole % based on the moles of n-butyl aldehyde.

In reaction steps (iii) and (iv) (i.e., reaction steps (i), (iii) and (iv)), the molar ratio between n-butyl aldehyde, 2-ethyl acrolein, formaldehyde and triethylamine totally charged was 1:0.2:3:0.1. Incidentally, the values of the molar ratio with respect to 2-ethyl acrolein and formaldehyde totally charged indicate respective values in molar ratio of 2-acrolein and formaldehyde totally charged in reaction step (iii) (i.e., reaction steps (i) and (iii)) relative to n-butyl aldehyde totally charged in the reaction step (iv) (i.e., reaction steps (i) and (iv)).

Subsequently, in the case where reaction steps (i) to (iii) were repeatedly conducted by regarding the reaction step (iv) as identical to the reaction step (i), ii was confirmed that the afore-mentioned molar ratio between n-butyl aldehyde, 2-ethyl acrolein, formaldehyde and triethylamine totally charged in reaction steps (i) and (iii) was maintained and the reactions of the respective reaction steps could be conducted in a steady state.

Thus, when the process comprising at least reaction step (i) (including reaction step (iv)) and reaction step (iii) was conducted, the desired product was produced with a high yield even though the molar ratio of formaldehyde to n-butyl aldehyde totally charged was small.

EXAMPLE 2

17.8 g (208 mmol) of 35% aqueous formaldehyde solution and 10 g (139 mmol) of n-butyl aldehyde were charged into a 100 ml round bottom flask equipped with a reflux condenser. While heating the mixed solution at 40° C., 1.4 g (14 mmol) of triethylamine was dropped thereto. Thereafter, while maintaining the temperature of the mixed solution at 40° C., the reaction between n-butyl aldehyde and formaldehyde was conducted for one hour (reaction step (i)). At this time, the molar ratio between n-butyl aldehyde, formaldehyde and triethylamine charged was 1:1.5:0.1.

The percentage of conversion of n-butyl aldehyde was 92.4%; the total yield of 2,2'-bis(hydroxymethyl)butanal and formaldehyde adduct of 2,2'-bis(hydroxymethyl)butanal was 53.0 mole %; and the selectivity to these products was 57.5%. In addition, the yield of 2-ethyl acrolein was 20 mole %. In addition, the amount of residual formaldehyde was 23 mole % based on the moles of n-butyl aldehyde.

Subsequently, the resultant reaction solution was subjected to distillation at 90° C. under ordinary pressure to separate a fraction containing 2-ethyl acrolein therefrom (concentration: 98% by weight).

Next, the thus-separated fraction containing 1.65 g (20.8 mmol) of 2-ethyl acrolein was added to 17.8 g (208 mmol) of 35% aqueous formaldehyde solution. While heating the mixed solution to 40° C., 0.21 g (2.08 mmol) of triethylamine was added dropwise to the mixed solution. Thereafter, the temperature of the mixed solution was maintained at 40° C. for one hour to react 2-ethyl acrolein and formaldehyde with each other (reaction step (iii)). At this time, the molar ratio between 2-ethyl acrolein, formaldehyde and triethylamine charged was 1:10:0.1.

The yield of 2,2'-bis(hydroxymethyl)butanal was 60.8 mole %, the yield of a formaldehyde adduct of 2,2'-bis(hydroxymethyl)butanal was 9.5 mole %, and the total yield of these products was 70.3 mole % based on the weight of 2-ethyl acrolein.

Next, while maintaining the temperature of the resultant reaction solution at 40° C., 10 g (139 mmol) of n-butyl aldehyde was added to the reaction solution. Thereafter, 1.19 g (11.8 mmol) of triethylamine was added dropwise to the mixed solution, and then n-butyl aldehyde and the unreacted formaldehyde were reacted with each other at 40° C. for one hour (reaction step (iv)).

In reaction step (iv), the percentage of conversion of n-butyl aldehyde was 76.6%; the total yield of 2,2'-bis(hydroxymethyl)butanal and formaldehyde adduct of 2,2'-bis(hydroxymethyl)butanal was 68.4 mole %; and the total selectivity to these products was 89.3%. At that time, the yield of 2-ethyl acrolein was 13.4 mole %. Further, the amount of residual formaldehyde was 21.6 mole % based on the mole of n-butyl aldehyde.

In reaction step (iii) and reaction steps (i) plus (iv), the molar ratio between n-butyl aldehyde, 2-ethyl acrolein, formaldehyde and triethylamine totally charged was 1:0.15:1.5:0.1.

EXAMPLE 3

59.5 g (693 mmol) of 35% aqueous formaldehyde solution and 10 g (139 mmol) of n-butyl aldehyde were charged into a 100 ml round bottom flask equipped with a reflux condenser. While heating the mixed solution at 40° C., 1.4 g (14 mmol) of triethylamine was added dropwise thereto. Thereafter, while maintaining the temperature of the mixed solution at 40° C., the reaction between n-butyl aldehyde and formaldehyde was conducted for one hour (reaction step (i)). At this time, the molar ratio between n-butyl aldehyde, formaldehyde and triethylamine charged was 1:5:0.1.

The percentage of conversion of n-butyl aldehyde was 100% and the total yield of 2,2'-bis(hydroxymethyl)butanal and formaldehyde adduct of 2,2'-bis(hydroxymethyl)butanal was 65.8 mole %. In addition, the yield of 2-ethyl acrolein was 12 mole %. Further, the amount of residual formaldehyde was 300 mole % based on the mole of n-butyl aldehyde.

Subsequently, the resultant reaction solution was subjected to distillation under ordinary pressure to separate a fraction containing 2-ethyl acrolein therefrom (concentration: 98% by weight).

Next, the thus-separated fraction containing 1.1 g (13.9 mmol) of 2-ethyl acrolein was added to 59.3 g (693 mmol) of 35% aqueous formaldehyde solution. While heating the mixed solution at 40° C., 0.14 g (1.37 mmol) of triethylamine was added dropwise to the mixed solution. Thereafter, the temperature of the mixed solution was maintained at 40° C. for one hour to react 2-ethyl acrolein and formaldehyde with each other (reaction step (iii)). At this time, the molar ratio between 2-ethyl acrolein, formaldehyde and triethylamine charged was 1:50:0.1.

The total yield of 2,2'-bis(hydroxymethyl)butanal and the formaldehyde adduct thereof was 48.1 mole % based on the weight of 2-ethyl acrolein.

Next, while maintaining the temperature of the resultant reaction solution at 40° C., 10 g (139 mmol) of n-butyl aldehyde is added to the reaction solution. Thereafter, 1.26 g (12.5 mmol) of triethylamine was added dropwise to the mixed solution, and then n-butyl aldehyde and the unreacted formaldehyde were reacted with each other at 40° C. for one hour reaction step (iv)).

In reaction step (iv), the percentage of conversion of n-butyl aldehyde was 100% and the total yield of 2,2'-bis (hydroxymethyl)butanal and formaldehyde adduct of 2,2'-bis(hydroxymethyl)butanal was 78.9 mole %. At that time, the yield of 2-ethyl acrolein was 14.2 mole %. Further, the amount of residual formaldehyde was 300 mole % based on the moles of n-butyl aldehyde.

In reaction step (iii) and reaction steps (i) plus (iv), the molar ratio between n-butyl aldehyde, 2-ethyl acrolein, formaldehyde and triethylamine totally charged was 1:0.1:1.5:0.1.

Comparative Example 1

119 g (1.39 mol) of 35% aqueous formaldehyde solution and 10 g (139 mmol) of n-butyl aldehyde were charged into a 100 ml round bottom flask equipped with a reflux condenser. While heating the mixed solution at 40° C., 1.4 g (14 mmol) of triethylamine was added dropwise thereto. Thereafter, while maintaining the temperature of the mixed solution at 40° C., the reaction between n-butyl aldehyde and formaldehyde was conducted for one hour (reaction step (i)). At this time, the molar ratio between n-butyl aldehyde, formaldehyde and triethylamine all charged in reaction step (i) was 1:10:0.1.

The percentage of conversion of n-butyl aldehyde was 100% and the total yield of 2,2'-bis(hydroxymethyl)butanal and formaldehyde adduct of 2,2'-bis(hydroxymethyl)butanal was 88.7 mole %. At this time, the yield of 2-ethyl acrolein was 8 mole %. However, it was observed that the unreacted formaldehyde in the reaction solution amounted to about 850 mole % based on the moles of n-butyl aldehyde so that complicated procedures were required to remove the unreacted formaldehyde from the reaction solution. This removal of unreacted formaldehyde added a large load to the process, thereby rendering the process costly and disadvantageous.

EXAMPLE 4

72 g (1 mol) of n-butyl aldehyde and 300 g (3 mol) of 30% aqueous formaldehyde solution were charged into a reactor. While heating the mixed solution at 40° C., 20 g (0.1 mol) of 20% aqueous NaOH solution was added dropwise thereto. Thereafter, while maintaining the temperature of the mixed solution at 60° C., the reaction between n-butyl aldehyde and formaldehyde was conducted for one hour (reaction step (i)). At this time, the molar ratio between n-butyl aldehyde, formaldehyde and NaOH all charged in reaction step (i) was 1:3:0.1.

The percentage of conversion of n-butyl aldehyde was 94.4%; the total yield of 2,2'-bis(hydroxymethyl)butanal and formaldehyde adduct of 2,2'-bis(hydroxymethyl)butanal was 59.5 mole %; and the total selectivity to these products was 63.0%. At this time, the yield of 2-ethyl acrolein was 20.6 mole %. In addition, the amount of residual formaldehyde was 105 mole % based on the moles of n-butyl aldehyde. Next, the resultant reaction solution was subjected to distillation at 90° C. under ordinary pressure to separate a fraction containing 2-ethyl acrolein therefrom (concentration: 98% by weight).

The thus-separated fraction containing 17 g (0.2 mol) of 2-ethyl acrolein was added to 300 g (3 mol) of 30% aqueous formaldehyde solution. While heating the mixed solution at 40° C., 4 g (0.02 mol) of 20% aqueous NaOH solution was added dropwise to the mixed solution. Thereafter, the temperature of the mixed solution was maintained at 40° C. for one hour to react 2-ethyl acrolein and formaldehyde with each other (reaction step (iii)). At this time, the molar ratio between 2-ethyl acrolein, formaldehyde and NaOH charged was 1:15:0.1.

The total yield of 2,2'-bis(hydroxymethyl)butanal and formaldehyde adduct of 2,2'-bis(hydroxymethyl)butanal was 65.5 mole % based on the weight of 2-ethyl acrolein.

Next, while maintaining the temperature of the resultant reaction solution at 60° C., 72 g (1 mol) of n-butyl aldehyde was added to the reaction solution. Thereafter, 16 g (0.08 mol) of 20% aqueous NaOH solution was added dropwise to the mixed solution, and then n-butyl aldehyde and the unreacted formaldehyde were reacted with each other (reaction step (iv)).

In reaction step (iv), the percentage of conversion of n-butyl aldehyde was 95%; the total yield of 2,2'-bis(hydroxymethyl)butanal and formaldehyde adduct of 2,2'-bis(hydroxymethyl)butanal was 72.2 mole %; and the total selectivity to these products was 76%. At that time, the yield of 2-ethyl acrolein was 22.0 mole %. Further, the amount of residual formaldehyde was 99.9 mole % based on the moles of n-butyl aldehyde.

In reaction step (iii) and reaction steps (i) plus (iv), the molar ratio between n-butyl aldehyde, 2-ethyl acrolein, formaldehyde and NaOH totally charged was 1:0.2:3:0.1.

380 g of a 25 wt % 2,2'-bis(hydroxymethyl)butanal solution which were collected from the bottom of the distilling column of the above-mentioned acrolein separation step, were heated at 60° C. 154 g of a 31 wt % hydrogen peroxide solution (1.4 mole) were dropped to the heated solution for 2 hours and the oxidation reaction was continued for 5 hours to obtain 2,2'-bis(hydroxymethyl)butanoic acid. The yield of 2,2'-bis(hydroxymethyl)butanoic acid was 47 mole % based on the mole of n-butyl aldehyde spent in the reaction step (iv).

EXAMPLE 5

72 g (1 mol) of n-butyl aldehyde and 170 g (1.7 mol) of 30% aqueous formaldehyde solution were charged into a reactor. While heating the mixed solution at 40° C., 16 g (0.08 mol) of 20% aqueous NaOH solution was added dropwise thereto. Thereafter, while maintaining the temperature of the mixed solution at 60° C., the reaction between n-butyl aldehyde and formaldehyde was conducted for one hour (reaction step (i)). At this time, the molar ratio between n-butyl aldehyde, formaldehyde and NaOH was 1:1.7:0.08.

The percentage of conversion of n-butyl aldehyde was 76.6%; the total yield of 2,2'-bis(hydroxymethyl)butanal and formaldehyde adduct of 2,2'-bis(hydroxymethyl)butanal was 49.9 mole %; and the total selectivity to these products was 65.1%. In addition, the yield of 2-ethyl acrolein was 22 mole %. Further, the amount of residual formaldehyde was 35 mole % based on the moles of n-butyl aldehyde.

Next, the resultant reaction solution was subjected to distillation at 90° C. under ordinary pressure to separate a fraction containing 2-ethyl acrolein therefrom (concentration: 98% by weight).

The thus-separated fraction containing 15.8 g (0.2 mol) of 2-ethyl acrolein was added to 170 g (1.7 mol) of 30% aqueous formaldehyde solution. While heating the mixed solution at 40° C., 6 g (0.03 mol) of 20% aqueous NaOH solution was added dropwise to the mixed solution. Thereafter, the temperature of the mixed solution was maintained at 40° C. for one hour to react 2-ethyl acrolein and formaldehyde with each other (reaction step (iii)). At this time, the molar ratio between 2-ethyl acrolein, formaldehyde and NaOH charged was 1:8.5:0.1.

The total yield of 2,2'-bis(hydroxymethyl)butanal and formaldehyde adduct thereof was 69.7 mole % based on the weight of 2-ethyl acrolein.

Next, while maintaining the temperature of the resultant reaction solution at 60° C., 72 g (1 mol) of n-butyl aldehyde was added to the reaction solution. Thereafter, 10 g (0.05 mol) of 20% aqueous NaOH solution was added dropwise to the mixed solution, and then n-butyl aldehyde and the unreacted formaldehyde were reacted with each other (reaction step (iv)).

In reaction step (iv), the percentage of conversion of n-butyl aldehyde was 68.2%; the total yield of 2,2'-bis (hydroxymethyl)butanal and formaldehyde adduct of 2,2'-bis(hydroxymethyl)butanal was 53.1 mole %; and the total selectivity to these products was 77.9%. In addition, the yield of 2-ethyl acrolein was 14.6 mole %. Further, the amount of residual formaldehyde was 22 mole % based on the mole of n-butyl aldehyde.

In reaction step (iii) and reaction steps (i) plus (iv), the molar ratio between n-butyl aldehyde, 2-ethyl acrolein, formaldehyde and NaOH totally charged was 1:0.2:1.7:0.08.

What is claimed is:

1. A process for producing 2,2'-bis(hydroxymethyl) alkanal represented by the general formula (II):

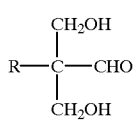

(II)

wherein R is a substituted or unsubstituted aliphatic hydrocarbon group, by reacting aliphatic aldehyde represented by general formula (I):

    (I)

wherein R is a substituted or unsubstituted aliphatic hydrocarbon group, with formaldehyde in the presence of a base catalyst, which comprises:

(i) reacting aliphatic aldehyde of general formula (I) with a formaldehyde-containing solution in the presence of a base catalyst to produce 2,2'-bis(hydroxymethyl) alkanal and as a by-product 2-substituted acrolein represented by the general formula (III):

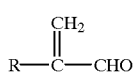

(III)

wherein R is a substituted or unsubstituted aliphatic hydrocarbon group; and (ii) reacting 2-substituted acrolein (III) produced in step (i) with formaldehyde in the presence of a base catalyst in a molar ratio of 2-substituted acrolein (III) to formaldehyde of 1:3 to 1:100 to produce 2,2'-bis (hydroxymethyl)alkanal, the molar ratio of the aliphatic aldehyde to formaldehyde totally charged to the overall process being in the range of 1:1 to 1:5.

2. A process according to claim 1, which comprises:

(i) reacting said aliphatic aldehyde (I) with a formaldehyde-containing solution in the presence of a base catalyst to produce 2,2'-bis(hydroxymethyl) alkanal and said 2-substituted acrolein (III);

(ii) separating 2-substituted acrolein (III) from the reaction mixture of step (i);

(iii) reacting separated 2-substituted acrolein (III) with formaldehyde in the presence of a base catalyst in a molar ratio of the 2-substituted acrolein (III) to formaldehyde of 1:3 to 1:100 to produce a formaldehyde-containing reaction mixture containing 2,2'-bis (hydroxymethyl)alkanal; and (iv) reacting at least a portion of then formaldehyde-containing reaction mixture obtained in step (iii) with the aliphatic aldehyde (I) in the presence of a base catalyst to produce 2,2'-bis(hydroxymethyl)alkanal.

3. A process according to claim 2, wherein the reaction step (iv) is identical to the reaction step (i) in which the formaldehyde-containing reaction solution obtained in reaction step (iii) is used as the formaldehyde-containing solution in reaction step (i), and the reaction steps (i) to (iii) are repeatedly conducted.

4. A process according to claim 1, wherein a portion of the reaction mixture produced in step (i) is separated into a component which is rich in 2,2'-bis(hydroxymethyl)alkanal and a component which is rich in 2-substituted acrolein, and the component which is rich in 2-substituted acrolein is reacted with formaldehyde in the presence of a base catalyst, followed by introducing the resultant reaction mixture to step (i), thereby continuously producing 2,2'-bis (hydroxymethyl)alkanal.

5. A process for producing 2,2'-bis(hydroxymethyl) alkanoic acid comprising oxidizing 2,2'-bis(hydroxymethyl) alkanal obtained by the process of claim 1.

6. A process according to claim 1, wherein the molar ratio of the aliphatic aldehyde to formaldehyde is in the range of 1:1 to 1:3.

7. A process according to claim 2, wherein the molar ratio of the aliphatic aldehyde to formaldehyde is in the range of 1:1 to 1:3.

8. A process according to claim 3, wherein the molar ratio of the aliphatic aldehyde to formaldehyde is in the range of 1:1 to 1:3.

9. A process according to claim 4, wherein the molar ratio of the aliphatic aldehyde to formaldehyde is in the range of 1:1 to 1:3.

10. A process according to claim 1, wherein the molar ratio of the 2-substituted acrolein (III) to formaldehyde is in the range of 1:3 to 1:50.

11. A process according to claim 2, wherein the molar ratio of the 2-substituted acrolein (III) to formaldehyde is in the range of 1:3 to 1:50.

12. A process according to claim 3, wherein the molar ratio of the 2-substituted acrolein (III) to formaldehyde is in the range of 1:3 to 1:50.

13. A process according to claim 4, wherein the molar ratio of the 2-substituted acrolein (III) to formaldehyde is in the range of 1:3 to 1:50.

14. A process according to claim 6, wherein the molar ratio of the 2-substituted acrolein (III) to formaldehyde is in the range of 1:3 to 1:50.

15. A process according to claim 7, wherein the molar ratio of the 2-substituted acrolein (III) to formaldehyde is in the range of 1:3 to 1:50.

16. A process according to claim 8, wherein the molar ratio of the 2-substituted acrolein (III) to formaldehyde is in the range of 1:3 to 1:50.

17. A process according to claim 9, wherein the molar ratio of the 2-substituted acrolein (III) to formaldehyde is in the range of 1:3 to 1:50.

* * * * *